United States Patent
MacDonald et al.

(10) Patent No.: US 11,793,446 B2
(45) Date of Patent: Oct. 24, 2023

(54) ELECTROANATOMICAL MAPPING SYSTEM WITH VISUALIZATION OF ENERGY-DELIVERY AND ELONGATED NEEDLE ASSEMBLIES

(71) Applicant: Boston Scientific Medical Device Limited, Galway (IE)

(72) Inventors: Matthew MacDonald, Calgary (CA); Charlene Leung, Scarborough (CA); Bryan Gellner, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 0 days.

(21) Appl. No.: 17/920,237

(22) PCT Filed: May 26, 2021

(86) PCT No.: PCT/IB2021/054590
§ 371 (c)(1),
(2) Date: Oct. 20, 2022

(87) PCT Pub. No.: WO2021/255556
PCT Pub. Date: Dec. 23, 2021

(65) Prior Publication Data
US 2023/0120097 A1    Apr. 20, 2023

Related U.S. Application Data

(60) Provisional application No. 63/040,052, filed on Jun. 17, 2020.

(51) Int. Cl.
*A61B 5/367*    (2021.01)
*A61B 5/339*    (2021.01)
(Continued)

(52) U.S. Cl.
CPC .............. *A61B 5/367* (2021.01); *A61B 5/262* (2021.01); *A61B 5/273* (2021.01); *A61B 5/339* (2021.01)

(58) Field of Classification Search
None
See application file for complete search history.

(56) References Cited

U.S. PATENT DOCUMENTS

| 175,254 A | 3/1876 | Oberly |
| 827,626 A | 7/1906 | Gillet |

(Continued)

FOREIGN PATENT DOCUMENTS

KR    10-1549786    9/2015

OTHER PUBLICATIONS

Written Opinion of the International Searching Authority, Korean Intellectual Property Office as International Searching Authority, three (3) pages, dated Sep. 1, 2021, Daejeon, Korea.

(Continued)

*Primary Examiner* — Kennedy Schaetzle
(74) *Attorney, Agent, or Firm* — Nelson Mullins Riley & Scarborough (57) ABSTRACT

Apparatus for use with an electroanatomical mapping system, an elongated needle assembly having a distal energy emitter configured to be detectable by the electroanatomical mapping system, an energy-delivery assembly having at least one sensor configured to receive, at least in part, the distal energy emitter of the elongated needle assembly in such a way that the distal energy emitter and said at least one sensor are movable relative to each other. The apparatus includes a signal-interface assembly. The signal-interface assembly includes a signal-input section configured to be signal connectable to said at least one sensor of the energy-delivery assembly. A signal-output section is configured to (Continued)

be signal connectable to an input section of the electroanatomical mapping system.

20 Claims, 7 Drawing Sheets

(51) Int. Cl.
*A61B 5/262* (2021.01)
*A61B 5/273* (2021.01)

(56) References Cited

U.S. PATENT DOCUMENTS

| | | |
|---|---|---|
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |

(56) References Cited

U.S. PATENT DOCUMENTS

| | | |
|---|---|---|
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | MaGuire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Molante et al. |
| 2004/0116851 A1 | 6/2004 | Johansen et al. |
| 2004/0127963 A1 | 7/2004 | Uchida et al. |
| 2004/0131299 A1* | 7/2004 | Adoram ............... A61B 8/0841 385/12 |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147837 A1 | 7/2004 | Macaulay et al. |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0090818 A1* | 4/2005 | Pike, Jr. ............. A61B 18/1492 606/41 |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0238985 A1* | 10/2007 | Smith ...................... A61B 5/06 600/424 |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0076476 A1 | 3/2009 | Barbagli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |

(56) References Cited

U.S. PATENT DOCUMENTS

| | | |
|---|---|---|
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0267840 A1 | 10/2013 | Markowitz et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |
| 2018/0078172 A1* | 3/2018 | Kusumoto ............ A61B 5/287 |
| 2019/0021763 A1 | 1/2019 | Zhou et al. |
| 2019/0247035 A1 | 8/2019 | Gittard et al. |
| 2020/0155031 A1 | 5/2020 | Jais et al. |
| 2021/0307671 A1* | 10/2021 | Leung .................... G06T 11/00 |

OTHER PUBLICATIONS

International Search Report and Written Opinion received for PCT Patent Application No. PCT/IB2021/054590, dated Sep. 1, 2021, 7 pages.

* cited by examiner

| Sensor No. | 901 Socket No. | Sheath Visualization | Dilator Visualization | Needle Visualization |
|---|---|---|---|---|
| 203D | 1 | 203D | | |
| 203C | 2 | 203C | | |
| 203B | 3 | 203B | | |
| 203A | 4 | 203A | | |
| 203A | 5 | | 203A | |
| 205 | 6 | | 205 | |
| 205 | 7 | | | 205 |
| 208 | 8 | | | 208 |

| Sensor No. | 901 Socket No. | Sheath Visualization | Dilator Visualization | Needle Visualization |
|---|---|---|---|---|
| 203D | 1 | 203D | | |
| 203C | 2 | 203C | | |
| 203B | 3 | 203B | | |
| 203A | 4 | 203A | | |
| 203B | 5 | | 203B | |
| 203A | 6 | | 203A | |
| 205 | 7 | | 205 | |
| 205 | 8 | | | 205 |
| 208 | 9 | | | 208 |

FIG. 9

ELECTROANATOMICAL MAPPING SYSTEM WITH VISUALIZATION OF ENERGY-DELIVERY AND ELONGATED NEEDLE ASSEMBLIES

TECHNICAL FIELD

This document relates to the technical field of (and is not limited to): (A) a signal-interface assembly for an electroanatomical mapping system (and/or a method associated therewith); and/or (B) an energy-delivery assembly having a sensor configured to be interfaced to a signal-input section of the signal-interface assembly of an electroanatomical mapping system (and/or a method associated therewith); and/or (C) a synergistic combination of an electroanatomical mapping system, an elongated needle assembly, an energy-delivery assembly and a signal-interface assembly (and/or a method associated therewith).

BACKGROUND

Known medical devices are configured to facilitate a medical procedure, and help healthcare providers diagnose and/or treat medical conditions of sick patients.

SUMMARY

It will be appreciated that there exists a need to mitigate (at least in part) at least one problem associated with the existing (known) electroanatomical mapping systems. After much study of, and experimentation with, existing (known) electroanatomical mapping systems, an understanding (at least in part) of the problem and its solution have been identified (at least in part) and are articulated (at least in part) as follows:

Electroanatomic mapping refers to the acquisition and display (via a display device) of electrical information (signals) pertaining to (derived or sensed from) a biological feature of a patient in combination with spatial localization (a visual map) of a biological feature (this is done, preferably, in situ). An electroanatomical mapping system (EAM system) is configured to provide a display device configured to show (map out and indicate, preferably in real time or near real time, in situ) the three-dimensional anatomy of a biological feature (such as the heart, etc.) of the patient.

It is known that electroanatomical mapping systems may utilize magnetic sensors and/or electrical impedance sensors for generating anatomical maps. Moreover, known transcatheter interventional procedures are utilized for the treatment of a biological feature (such as the left side of the heart) of the patient. For instance, a known procedure among these is the pulmonary vein isolation (PVI) procedure that utilizes an ablation catheter by way of selective application (emission) of radio-frequency energy to a desired portion of the biological feature (such as, a biological wall, etc.). The known PVI procedure may be executed (performed) with assistance from an electroanatomical mapping system configured to visualize both the left atrium (of the heart) and the ablation catheter (preferably, this is done simultaneously and in situ). While under visualization (via the display device of the electroanatomical mapping system), a medical device (which transports the ablation catheter) may be maneuvered and/or navigated (preferably in situ) in such a way that the ablation catheter may be maneuvered to a desired biological feature (or a biological site) of the patient; once the desired biological site is located (by identification via the display device), and the ablation catheter is suitably positioned proximate to (or in contact with) the desired biological site (as indicated by the display device), radio-frequency ablation may be activated (via the ablation catheter) for formation of a desired lesion at the desired biological site.

It may be desirable to accomplish a procedure with less time and/or with more certainty, thereby reducing, at least in part, labor costs, operating room time, etc., associated with executing the procedure.

It may be desirable to provide, for the electroanatomical mapping system, a medical sheath assembly (which is steerable within the patient) configured to improve the procedural workflow of a procedure, such as the known PVI procedure, by allowing a medical device (such as a medical sheath assembly, etc.) to be visualized (in situ) along with an ablation device (such as an ablation catheter, etc.) via the display device of the electroanatomical mapping system.

Before an ablation procedure may be carried out, a transseptal puncture may be required to access the left atrium of the heart. This portion of the procedure may be very difficult to be properly, and confidently, visualized using the display device of the electroanatomical mapping system.

It may be desirable to provide, to users (such as electrophysiologists), an apparatus configured to enable visualization of a radio-frequency transseptal puncture needle by the electroanatomical mapping system.

It may be desirable to provide, for a procedure using energy puncturing, a signal switch assembly (an electrical switch box) configured to convey information (such as voltage measurements, etc.) from at least one medical device (such as, a combination of an ablation catheter and/or a medical sheath assembly) to the electroanatomical mapping system.

For instance, electrophysiologists may rely on a mix of ultrasound, such as, Intracardiac Echocardiography (ICE) and/or Transesophageal Echocardiography (TEE) and fluoroscopy to perform the transseptal puncture (preferably, in situ); these types of equipment may be, disadvantageously, very expensive to own, maintain and/or operate.

It may be desirable to perform the transseptal puncture by utilizing the electroanatomical mapping system. In this manner, the user may, advantageously, receive less (preferably no) or limited x-ray radiation from fluoroscopy, which may be a high priority; moreover, significant capital cost might be avoiding ultrasound technologies altogether.

It may be desirable to provide a steerable sheath assembly with sensors (such as electrodes) using the electroanatomical mapping system. It will be appreciated that a device may be needed for various sensor combinations deployed on the medical devices.

It may be desirable to share sensors of a combination of medical devices (such as a sheath assembly, an energy puncture device, etc.) for visualization of the medical devices via the display device of the electroanatomical mapping system.

It may be desirable to provide electroanatomic mapping based on the acquisition and display (via a display device) of electrical information (signals) pertaining to (derived or sensed from) a biological feature of a patient in combination with spatial localization (a visual map) of the biological feature along with at least one sensor (or two or more sensors) associated with at least one medical assembly such as a catheter (or two or more medical assemblies); this is done, preferably, in situ (during a procedure).

To mitigate, at least in part, at least one problem associated with the existing technology, there is provided (in accordance with a major aspect) an apparatus. The apparatus is for use with an electroanatomical mapping system, an elongated needle assembly (having a distal energy emitter configured to be detectable by the electroanatomical mapping system), an energy-delivery assembly (having at least one sensor configured to receive, at least in part, the distal energy emitter of the elongated needle assembly; this is done in such a way that the distal energy emitter and the sensor are movable relative to each other). The apparatus includes and is not limited to a signal-interface assembly including a signal-input section. The signal-input section is configured to be signal connectable to the sensor of the energy-delivery assembly. The signal-interface assembly also includes a signal-output section configured to be signal connectable to an input section of the electroanatomical mapping system. The electroanatomical mapping system is configured to display, via a display device, a spatial positioning of the sensor of the energy-delivery assembly along with the distal energy emitter (of the elongated needle assembly); this is done, preferably, after: (A) the signal-input section, in use, is signal connected to the sensor of the energy-delivery assembly; and (B) the signal-output section, in use, is signal connected to the input section of the electroanatomical mapping system.

To mitigate, at least in part, at least one problem associated with the existing technology, there is provided (in accordance with a major aspect) an apparatus. The apparatus is for use with an electroanatomical mapping system (including a signal-interface assembly), and is also for use with an elongated needle assembly (having a distal energy emitter configured to be detectable by the electroanatomical mapping system). The apparatus includes and is not limited to an energy-delivery assembly having at least one sensor configured to receive, at least in part, the distal energy emitter of the elongated needle assembly; this is done in such a way that the distal energy emitter and the sensor are movable relative to each other. The sensor is also configured to be interfaced to a signal-input section of the signal-interface assembly. The electroanatomical mapping system is configured to display, via a display device, spatial positioning of the sensor of the energy-delivery assembly along with the distal energy emitter of the elongated needle assembly; this is done, preferably, after: (A) the signal-interface assembly, in use, is signal connected to said at least one sensor of the energy-delivery assembly; and (B) the signal-interface assembly, in use, is signal connected to the input section of the electroanatomical mapping system.

To mitigate, at least in part, at least one problem associated with the existing technology, there is provided (in accordance with a major aspect) a method. The method is for operating an electroanatomical mapping system (having a signal-interface assembly), an elongated needle assembly (having a distal energy emitter configured to be detectable by the electroanatomical mapping system), an energy-delivery assembly (having at least one sensor configured to receive, at least in part, the distal energy emitter of the elongated needle assembly; this is done in such a way that the distal energy emitter and the sensor are movable relative to each other). The method includes displaying, via a display device of the electroanatomical mapping system, spatial positioning of the sensor of the energy-delivery assembly along with the distal energy emitter (of the elongated needle assembly); this is done, preferably, after: (A) the signal-input section, in use, is signal connected to the sensor of the energy-delivery assembly; and (B) the signal-output section, in use, is signal connected to the input section of the electroanatomical mapping system.

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not depicted to provide a less obstructed view of the embodiments of the present disclosure.

LISTING OF REFERENCE NUMERALS
USED IN THE DRAWINGS energy-delivery assembly 201
medical sheath assembly 202
sheath sensors (203A, 203B, 203C, 203D)
medical dilator assembly 204
dilator sensor 205
needle assembly 206
distal energy emitter 208
travel path 209
wire 210
sheath lumen 211
connection 212
energy generator 214
sensor wires 216
handle assembly 500
sheath steering adjustment knob 502
handle extension 504
needle handle 506
conductor cable 508
extension cable 510
switch box 512
mapping cable 514
sheath side port tube 516
sheath conductor cable 518
first electrical wire 813A
second electrical wire 815
first electrical contact 833
second electrical contact 835
electrical commutator device 836
electroanatomical mapping system 900
signal-interface assembly 901
mapping cable 520
hub 522
conductor 524
handle assembly 600
steering adjustment knob 602
handle extension 604
needle handle 606
energy cable 608
extension cable 610
switch-box assembly 612
energy port 613
sensor-signal port 614
sheath side port tube 616
sheath wire assembly 618
sheath extension cable 619
mapping cable 620
hub 622
conductor 624
pins (703A, 703B, 703C, 703D, 705, 708)
sheath image 802
dilator image 804
needle image 806
puncture-device image 808
display device 902
sockets 905
signal-input section 910
signal-output section 912
first internal jumper 1002
second internal jumper 1004

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

Figure 1:
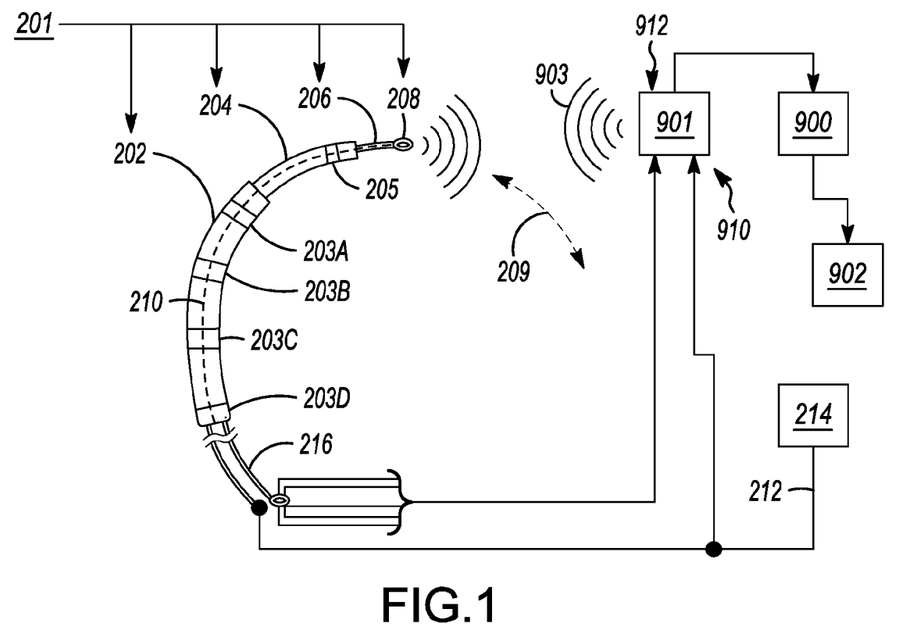
FIG. 1 depicts a schematic view of an embodiment of a signal-interface assembly of an electroanatomical mapping system.

FIG. 1 depicts a schematic view of an embodiment of a signal-interface assembly 901 of an electroanatomical mapping system 900.

Referring to the embodiment as depicted in FIG. 1, an energy-delivery assembly 201 includes a distal energy emitter 208. The energy-delivery assembly 201 is configured to be inserted into, and movable along, a confined space defined by a living body (the patient). Movement of the energy-delivery assembly 201 is to be controlled by a user (by such means as a steering device, etc., not depicted but are known to persons of skill in the art and therefore not described). The energy-delivery assembly 201 is configured to maneuver, and position, the distal energy emitter 208 proximate to the biological feature of the patient. The energy-delivery assembly 201 is configured to maneuver and position the distal energy emitter 208 along a travel path 209. The distal energy emitter 208 is configured to selectively emit energy (once activated for the formation of a puncture through a biological feature of the patient) after the energy-delivery assembly 201 has positioned the distal energy emitter 208 proximate to the biological feature of the patient. The distal energy emitter 208 is configured to form a puncture once activated to emit energy therefrom, such as radio-frequency energy, etc., and any equivalent thereof. The distal energy emitter 208 may include any type of energy-emitting device, etc.

Referring to the embodiment as depicted in FIG. 1, an energy-delivery assembly 201 includes biocompatible material properties suitable for sufficient performance (dielectric strength, thermal performance, insulation and corrosion, water and/or heat resistance, etc.) to comply with industrial and/or regulatory safety standards (or compatible for medical usage in general). Reference is made to the following publication for consideration in the selection of a suitable material: Plastics in Medical Devices: Properties, Requirements, and Applications; 2nd Edition; author: Vinny R. Sastri; hardcover ISBN: 9781455732012; published: 21 Nov. 2013; publisher: Amsterdam [Pays-Bas]: Elsevier/William Andrew, [2014].

Referring to the embodiment as depicted in FIG. 1, the energy-delivery assembly 201 includes (and is not limited to) a synergistic combination of an elongated needle assembly 206, a medical sheath assembly 202, and a medical dilator assembly 204. The elongated needle assembly 206 is configured to be received within, and along, an elongated dilator lumen of (defined by) the medical dilator assembly 204. The medical dilator assembly 204 is configured to be received (at least in part), within and along, the lumen of the medical sheath assembly 202. The elongated needle assembly 206 extends from the distal energy emitter 208. The medical sheath assembly 202 has at least one sheath sensor mounted thereto (such as, spaced-apart sheath sensors 203A, 203B, 203C, 203D, etc.) and positioned along predetermined spaced-apart positions located along an elongated length of the medical sheath assembly 202. The medical dilator assembly 204 has at least one dilator sensor (205) positioned (preferably) at the distal end of the medical dilator assembly 204. A wire 210 is electrically connected to the distal energy emitter 208. The wire 210 extends along a longitudinal length of the elongated needle assembly 206 (from the distal end to the proximal end thereof). A set of sensor wires 216 is electrically connected to respective (one for each of the) sheath sensors (203A, 203B, 203C, 203D) and to the dilator sensor 205.

Referring to the embodiment as depicted in FIG. 1, the wire 210 extends along a length of the energy-delivery assembly 201 (preferably along the interior thereof) between a proximal end and a distal end of the energy-delivery assembly 201. At the distal end of the energy-delivery assembly 201, the wire 210 is electrically connected to the distal energy emitter 208. At the proximal end of the energy-delivery assembly 201, the wire 210 is configured to be electrically connectable to an energy generator 214 (via a connection 212). The energy generator 214 is configured to selectively generate, and output, energy (such as radio-frequency energy) that is conveyed to the distal energy emitter 208 (via the wire 210 and the connection 212, etc.). The energy generator 214 may include a radio frequency-energy generator, etc., and any equivalent thereof.

Referring to the embodiment as depicted in FIG. 1, the energy-delivery assembly 201 and the distal energy emitter 208 may, for instance, include (and are not limited to) a radio frequency puncture device, such as the BAYLIS (TRADEMARK) POWERWIRE (REGISTERED TRADEMARK) radio frequency guidewire manufactured by BAYLIS MEDICAL COMPANY (headquartered in Canada).

Referring to the embodiment as depicted in FIG. 1, the electroanatomical mapping system 900 may include fluoroscopy mapping systems (if so desired, but may not be preferred for some embodiments). The electroanatomical mapping system 900 includes, preferably, a nonfluoroscopy mapping system, such as, and not limited to, (A) the CARTO EP (TRADEMARK) mapping system (manufactured by BIOSENSE WEBSTER based in the USA), (B) the ENSITE PRECISION (TRADEMARK) cardiac mapping system (manufactured by Abbott Laboratories based in the USA), (C) the LOCALISA (TRADEMARK) intracardiac mapping system (manufactured by MEDTRONICS INC., based in the USA), and (D) the RHYTHMIA HDx (TRADEMARK) mapping system (manufactured by Boston Scientific Corp., based in the USA).

Referring to the embodiment as depicted in FIG. 1, the signal-interface assembly 901 is configured to be electrically connectable (via a wire and/or wirelessly, directly or indirectly, etc.) to the electroanatomical mapping system 900. The signal-interface assembly 901 may include, for instance, a pin box, a housing having an array of receivers (sockets) configured to receive plugs (wired plugs), etc., and any equivalent thereof. The signal-interface assembly 901 may be configured for conveying any type of signal, such as an electro-magnetic signal, an electrical signal and/or a magnetic signal, etc., and any equivalent thereof. The signal-interface assembly 901 is configured to receive signals from the sensors (203A, 203B, 203C, 203D, 205) of the energy-delivery assembly 201. In addition, the signal-interface assembly 901 is configured to receive (at least in part) the signal from the energy generator 214 (which may be the same or a similar energy signal provided to the distal energy emitter 208 of the energy-delivery assembly 201). The distal energy emitter 208 is configured to be activated. The sheath sensors (203A, 203B, 203C, 203D) and the dilator sensor 205 (and the activated distal energy emitter 208) are all configured to be detectable by the electroanatomical mapping system 900 (via the signal-interface assembly 901 and/or by other types of sensing devices, not depicted and known to persons skilled in the art, such as magnetic devices and/or electrical impedance devices, etc., and any equivalent thereof).

Referring to the embodiment as depicted in FIG. 1, the display device 902 is configured to be electrically connected to the electroanatomical mapping system 900. The electroanatomical mapping system 900 is configured to output (in use) mapping information (visual representation data) to the display device 902, in which the mapping information may include relative spatial positions of the distal energy emitter 208 (once activated), the sheath sensors (203A, 203B, 203C, 203D) and the dilator sensor 205, during a procedure (in situ). In this arrangement, the user is provided with additional visual information (of medical devices inserted into the patient) so that the user may make improved (or better) procedural decisions during the procedure.

Figure 2:
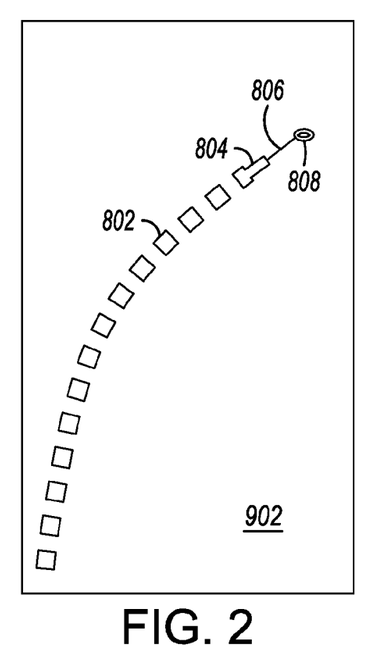
FIG. 2 and FIG. 3 depict schematic views of embodiments of a display device of the electroanatomical mapping system of FIG. 1.
Figure 3:
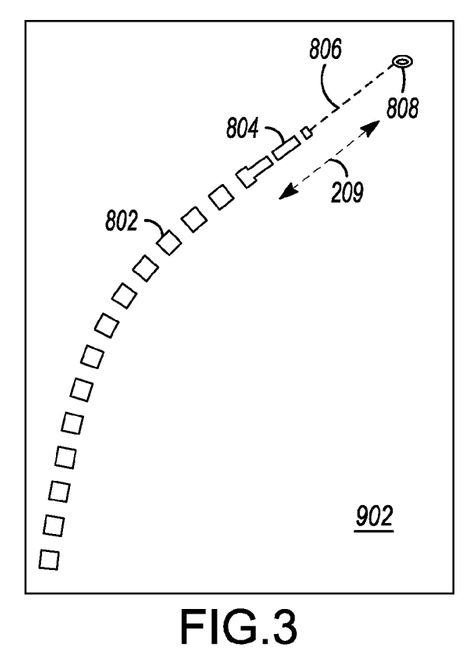

Referring to the embodiment as depicted in FIG. 1, the energy-delivery assembly 201 is configured to be enabled for use with the electroanatomical mapping system 900. The energy-delivery assembly 201 and the electroanatomical mapping system 900 may be utilized for any type of procedure, such as the transseptal puncture procedure portion of a procedure. The technical effect of the energy-delivery assembly 201 and/or the signal-interface assembly 901 is provision of improved (expanded) visualization of the medical devices inserted in the body of the patient (such as the energy-delivery assembly 201) during a procedure. The energy-delivery assembly 201 includes sensors configured to be detected by the electroanatomical mapping system 900; this is done in such a way that the electroanatomical mapping system 900 may provide a visual map (mapping data) to the display device 902 (based on sensor data received by the signal-interface assembly 901). For instance, the energy-delivery assembly 201 may provide a tool for locating the ideal location on a biological feature (such as, the septum and/or the foramen ovale), aligning a puncture angle, and confirming contact with, and/or the tenting of, a biological wall before application of energy to the tissue via the distal energy emitter 208. The physician (user) may be able to see (visualize) the energy-delivery assembly 201 via the display device 902, preferably as in-line, coaxial catheters, much as they might appear to the eye of the user, as depicted in FIG. 2 and FIG. 3.

Referring to the embodiment as depicted in FIG. 1, there is depicted an apparatus for use with the electroanatomical mapping system 900, the elongated needle assembly 206 (having the distal energy emitter 208 configured to be detectable by the electroanatomical mapping system 900), and the energy-delivery assembly 201 (having at least one sensor configured to receive, at least in part, the distal energy emitter 208 of the elongated needle assembly 206; this is done in such a way that the distal energy emitter 208 and the sensor are movable relative to each other). The apparatus includes and is not limited to (comprises) a signal-interface assembly 901. The signal-interface assembly 901 includes a signal-input section 910 configured to be signal connectable to the sensor of the energy-delivery assembly 201. The signal-interface assembly 901 also includes a signal-output section 912 configured to be signal connectable to an input section of the electroanatomical mapping system 900. The electroanatomical mapping system 900 is configured to display, via the display device 902, spatial positions of the sensor of the energy-delivery assembly 201 along with the distal energy emitter 208 of the elongated needle assembly 206; this is done, preferably, after: (A) the signal-input section 910, in use, is signal connected to the sensor of the energy-delivery assembly 201; and (B) the signal-output section 912, in use, is signal connected to the input section of the electroanatomical mapping system 900.

Referring to the embodiment as depicted in FIG. 1, there is depicted an apparatus for use with the electroanatomical mapping system 900 (including the signal-interface assembly 901). The apparatus is also for use with the elongated needle assembly 206 (having the distal energy emitter 208 configured to be detectable by the electroanatomical mapping system 900). The apparatus includes and is not limited to (comprises) the energy-delivery assembly 201 having at least one sensor configured to receive, at least in part, the distal energy emitter 208 of the elongated needle assembly 206 (this is done in such a way that the distal energy emitter 208 and the sensor are movable relative to each other). The sensor is also configured to be interfaced to a signal-input section 910 of the signal-interface assembly 901. The electroanatomical mapping system 900 is configured to display, via a display device, spatial positions of the sensor of the energy-delivery assembly 201 along with the distal energy emitter 208 (of the elongated needle assembly 206); this is done, preferably, after: (A) the signal-interface assembly 901, in use, is signal connected to said at least one sensor of the energy-delivery assembly 201; and (B) the signal-interface assembly 901, in use, is signal connected to the input section of the electroanatomical mapping system 900.

Referring to the embodiment as depicted in FIG. 1, there is depicted an apparatus that includes and is not limited to (comprises) a synergistic combination of the electroanatomical mapping system 900, the elongated needle assembly 206, the energy-delivery assembly 201 and the signal-interface assembly 901.

FIG. 2 and FIG. 3 depict schematic views of embodiments of a display device 902 of the electroanatomical mapping system 900 of FIG. 1.

Referring to the embodiments as depicted in FIG. 2 and FIG. 3, the display device 902 provides (in use) the visualization map (also called mapping information). The visualization map, for instance, indicates: (A) a sheath image 802 of (representing) the medical sheath assembly 202 (as depicted in FIG. 1); (B) a dilator image 804 of (representing) the medical dilator assembly 204 (as depicted in FIG. 1); (C) an elongated needle image 806 of (representing) the elongated needle assembly 206 (of FIG. 1); and (D) a puncture-device image 808 of (representing) the distal energy emitter 208 (of FIG. 1).

Referring to the embodiment as depicted in FIG. 2, the display device 902 depicts the mapping information in which the visual representation (as depicted) implies (infers) that the image representing the distal energy emitter 208 is depicted as being positioned relatively closer to (retracted within) the distal end portion of the image representing the energy-delivery assembly 201.

Referring to the embodiment as depicted in FIG. 3, the display device 902 depicts the mapping information. The visual imaging representation (as depicted) implies (infers) the distal energy emitter 208 is positioned relatively further away from (extended away from) the distal end portion of the energy-delivery assembly 201. The distal energy emitter 208 may be visualized as being movable along the travel path 209 or movement direction (by referring to the movement of the puncture-device image 808).

Figure 4:
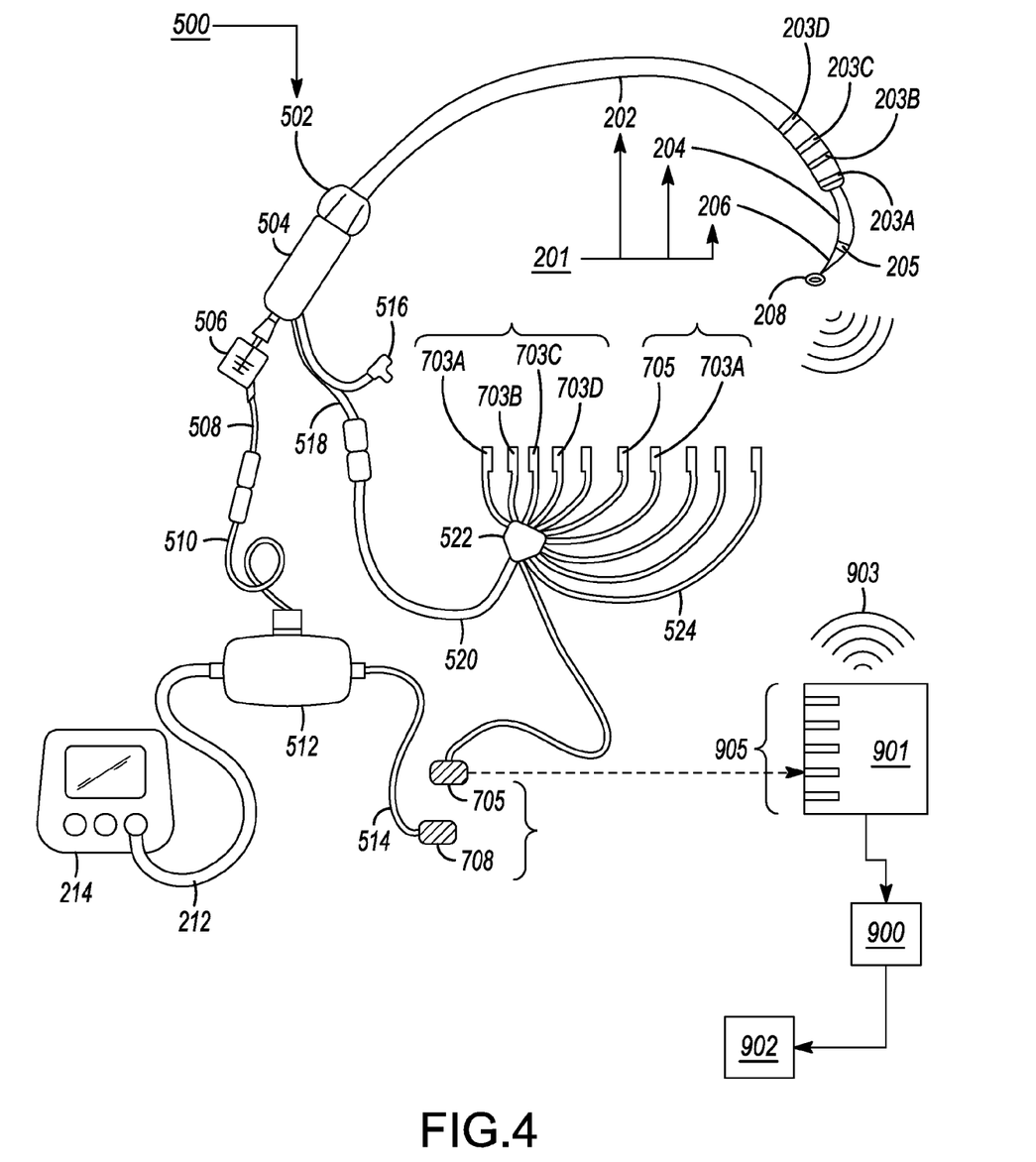
FIG. 4 depicts a schematic view of an embodiment of the signal-interface assembly of the electroanatomical mapping system of FIG. 1.

FIG. 4 depicts a schematic view of an embodiment of the signal-interface assembly 901 of the electroanatomical mapping system 900 of FIG. 1.

Referring to the embodiment as depicted in FIG. 4, there is depicted a handle assembly 500. It will be appreciated that some of the items (or components) of the handle assembly 500 are known to persons skilled in the art (such as, a steering device, etc.), and as such, these items are not described in detail.

Referring to the embodiment as depicted in FIG. 4, the handle assembly 500 includes a sheath steering adjustment knob 502, a handle extension 504, a needle handle 506 and a conductor cable 508. The conductor cable 508 is configured to convey energy to the distal energy emitter 208 (once connected accordingly to the energy generator 214, etc.). The handle assembly 500 also includes an extension cable 510 for the conductor cable 508. The handle assembly 500 also includes a switch box 512. The switch box 512 is configured to connect (split) the signals between the energy generator 214 to (A) the distal energy emitter 208 (via the conductor cable 508, etc.), and (B) the signal-interface assembly 901 (via the mapping cable 514). The mapping cable 514 is configured to convey the energy signal of the energy generator 214 to the signal-interface assembly 901.

Referring to the embodiment as depicted in FIG. 4, the handle assembly 500 also includes a sheath side port tube 516. The handle assembly 500 also includes a sheath conductor cable 518. The sheath conductor cable 518 is configured to convey the signals from the sensors (203A, 203B, 203C, 203D, 205) to the signal-interface assembly 901 (via specific or predetermined conductors, etc.). The sheath conductor cable 518 is configured to electrically connect to a mapping cable 520. A hub 522 extends from an end section of the mapping cable 520. A dedicated conductor 524 extends from the hub 522 of the mapping cable 520. The mapping cable 520 is configured to split into multiple conductors each (respectively) having a dedicated pin (703A, 703B, 703C, 703D, 705) also called plugs, etc. Each of the pins (703A, 703B, 703C, 703D, 705) is configured to be inserted into a respective dedicated socket (portal, receiver) of the signal-interface assembly 901. The pins (703A, 703B, 703C, 703D) are configured to be electrically respectively connectable to a dedicated socket of the signal-interface assembly 901, and are configured (respectively) to convey sensor signals from the sensors (203A, 203B, 203C, 203D, 205) to the signal-interface assembly 901. The pin 708 is connected to the mapping cable 514. The pin 708 is configured to (A) be electrically connectable to a dedicated socket of the signal-interface assembly 901, and (B) (respectively) convey (at least in part) the energy signal from the energy generator 214 to the signal-interface assembly 901 (which is the energy signal also sent to the distal energy emitter 208).

Referring to the embodiment as depicted in FIG. 4, the energy generator 214 is configured to be electrically connectable to the distal energy emitter 208 and to the signal-interface assembly 901 via the connection 212 and the switch box 512, etc. The signal-interface assembly 901 includes an array of sockets 905 configured to be electrically connectable to the pins (703A, 703B, 703C, 703D, 705, 708). The pins (703A, 703B, 703C, 703D, 705, 708) are assigned (preferably) into groupings. The pins (703A, 703B, 703C, 703D) are assigned to a first pin group so that the signal-interface assembly 901 may convey these signals to the electroanatomical mapping system 900 to represent signals associated with a first aspect of the energy-delivery assembly 201 (such as, a length of a portion of the medical sheath assembly 202 of the energy-delivery assembly 201, etc.). The pins (703A, 705) are assigned to a second pin group so that the signal-interface assembly 901 may convey these signals to the electroanatomical mapping system 900 to represent signals associated with a second aspect of the energy-delivery assembly 201 (such as, the relative separation distance between the distal tips of the medical sheath assembly 202 and the medical dilator assembly 204). The pins (705, 708) are assigned to a third pin group so that the signal-interface assembly 901 may convey these signals to the electroanatomical mapping system 900 to represent signals associated with a third aspect of the energy-delivery assembly 201 (such as, the relative separation distance between the distal tip of the medical dilator assembly 204 and the distal energy emitter 208 positioned at the distal end of the elongated needle assembly 206, etc.).

Referring to the embodiment as depicted in FIG. 4, it will be appreciated that a use of the signal-interface assembly 901 may include the mapping visualization of the medical sheath assembly 202, the medical dilator assembly 204 and the elongated needle assembly 206 (to be depicted on the display device 902, during a procedure, such as the transseptal puncture procedure); it will be appreciated that, preferably, the signal-interface assembly 901 is a way to replace and/or supplement the use of the intracardiac echo system and/or the fluoroscopy system, etc., if so desired.

Referring to the embodiment as depicted in FIG. 4, the signal-interface assembly 901 is configured to electrically convey (in use) electrical signals from aspects of the energy-delivery assembly 201 to enable visualization of at least one aspect (geometrical visual aspect) of the energy-delivery assembly 201 via the display device 902 of the electroanatomical mapping system 900. The mapping software of the electroanatomical mapping system 900 is configured to receive and handle these signals in order to generate the visualization map to be displayed on the display device 902 (as depicted, for instance, in FIG. 2 and/or FIG. 3). The mapping software (programming) of the electroanatomical mapping system 900 may be configured to visually map out the alignment of the components of the energy-delivery assembly 201, etc., that may be utilized (by the user) for visually assisting the user during a procedure. Without using the signal-interface assembly 901, for instance, visualization of the alignment of the components of the energy-delivery assembly 201 may be more difficult to achieve (and prone to unwanted errors, etc.). The mapping software of the electroanatomical mapping system 900 may be configured to compute, and then display via the display device 902, the alignment of the components of the energy-delivery assembly 201.

Figure 5:
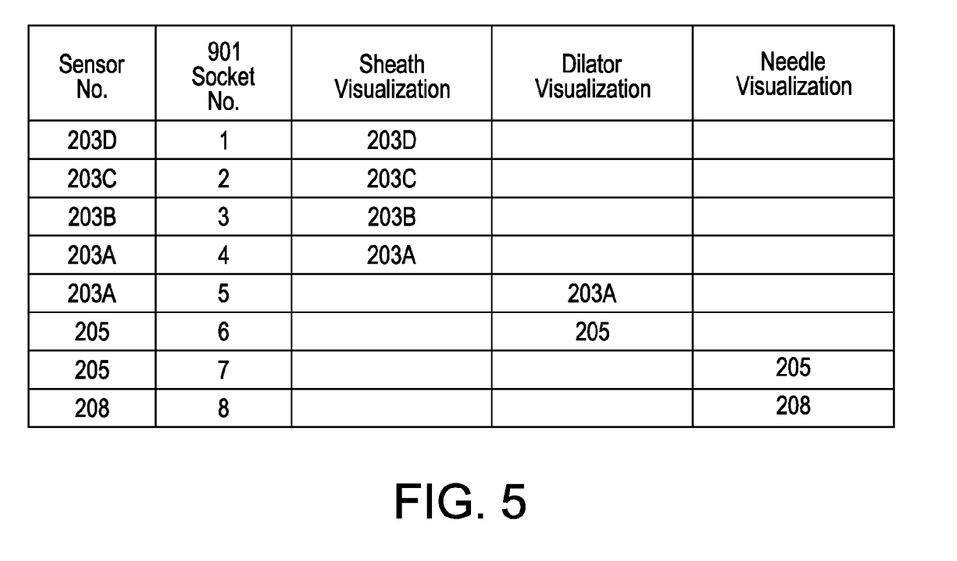
FIG. 5 depicts a schematic view of an embodiment of a configuration of the signal-interface assembly of FIG. 4.

FIG. 5 depicts a schematic view of an embodiment of a configuration of the signal-interface assembly 901 of FIG. 4.

Referring to the embodiment as depicted in FIG. 5, there is depicted an assignment of groupings for the sockets 905 of the signal-interface assembly 901 of FIG. 4. It will be appreciated that other configurations for, or variations of, the pairing or grouping of pins and sockets may be realized, as desired, in order to obtain and display different visual aspects of the energy-delivery assembly 201 (as may be needed for specific procedures).

Figure 6:
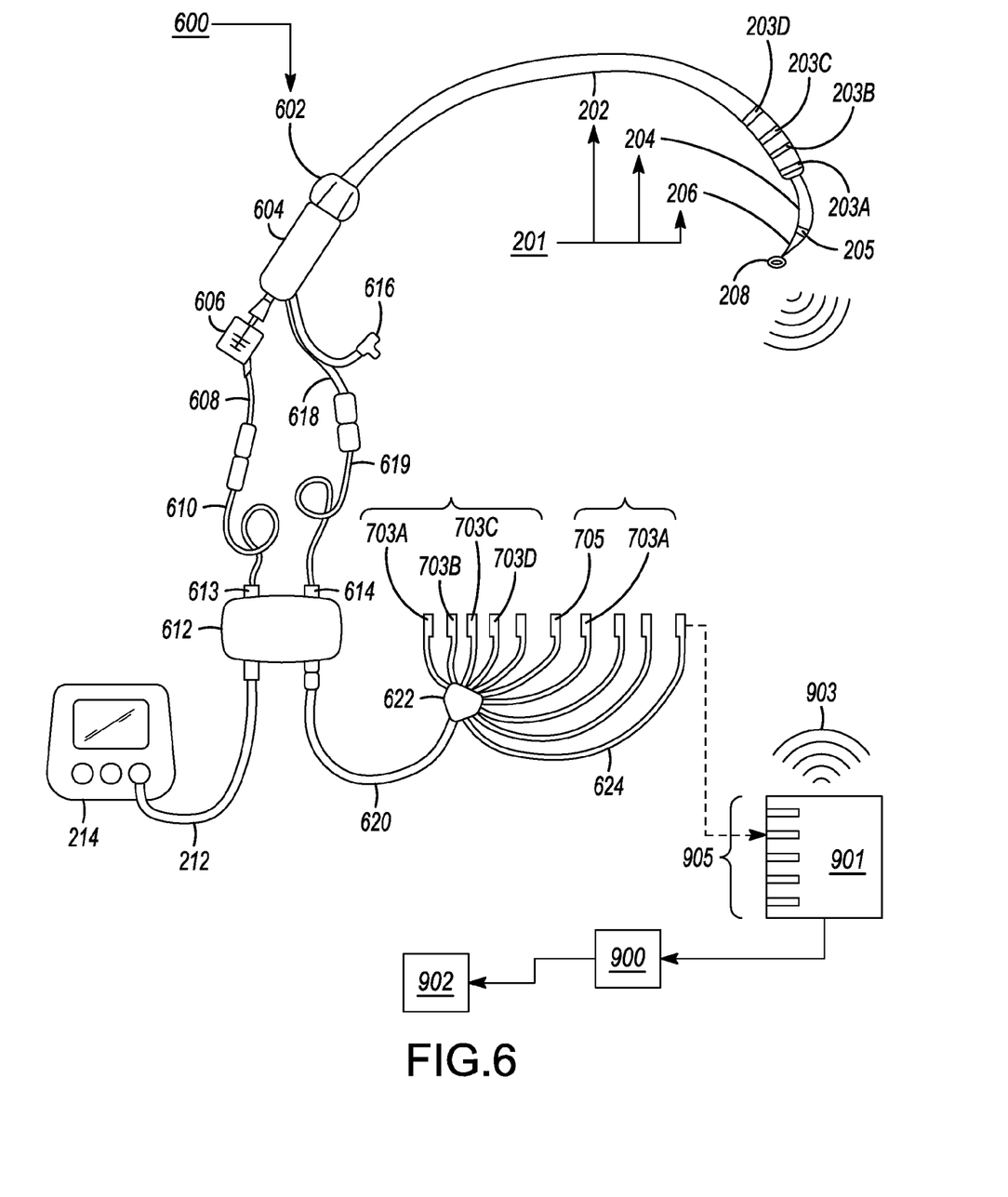
FIG. 6 depicts a schematic view of an embodiment of the signal-interface assembly of the electroanatomical mapping system of FIG. 1.

FIG. 6 depicts a schematic view of an embodiment of the signal-interface assembly 901 of the electroanatomical mapping system 900 of FIG. 1.

Referring to the embodiment as depicted in FIG. 6, there is depicted a handle assembly 600 including a steering adjustment knob 602, a handle extension 604, a needle handle 606, and an energy cable 608 (for conveying energy to the distal energy emitter 208). The handle assembly 600 also includes an extension cable 610 for the energy cable 608, etc.

Referring to the embodiment as depicted in FIG. 6, the handle assembly 600 also includes a switch-box assembly 612. The switch-box assembly 612 includes an energy port 613 configured to convey the energy signal from the connection 212 to the distal energy emitter 208 (via the extension cable 610, the energy cable 608, etc.).

Referring to the embodiment as depicted in FIG. 6, the handle assembly 600 also includes a sheath side port tube 616, and a sheath wire assembly 618. The sheath wire assembly 618 provides dedicated wires each respectively electrically connected to dedicated sensors (203A, 203B, 203C, 203D, 205). A sheath extension cable 619 connects to the sheath wire assembly 618 (for extending the sheath wire assembly 618, etc.).

Referring to the embodiment as depicted in FIG. 6, the switch-box assembly 612 includes a sensor-signal port 614. The sensor-signal port 614 is configured to electrically connect to the sheath wire assembly 618 (via the sheath extension cable 619), to a mapping cable 620, etc. A set of conductors extends from a hub 622 of the mapping cable 620. A conductor 624 extends from the hub 622. The mapping cable 620 splits into pins (703A, 703B, 703C, 703D, 705, 708). The pins (703A, 703B, 703C, 703D, 705, 708) are configured to electrically connect to respective sockets of the signal-interface assembly 901, and are configured to convey sensor signals of respective sensors (203A, 203B, 203C, 203D, 205) and the energy signal (to be applied to the distal energy emitter 208) from the energy generator 214 to the signal-interface assembly 901.

Referring to the embodiment as depicted in FIG. 6, the energy generator 214 is connectable to the distal energy emitter 208 via the connection 212. Advantageously, additional physical aspects of the energy-delivery assembly 201 may be visualized by utilizing the embodiment as depicted in FIG. 6. For instance, the curvature of the energy-delivery assembly 201 (or component thereof) may be better visualized (more accurately).

Figure 7:
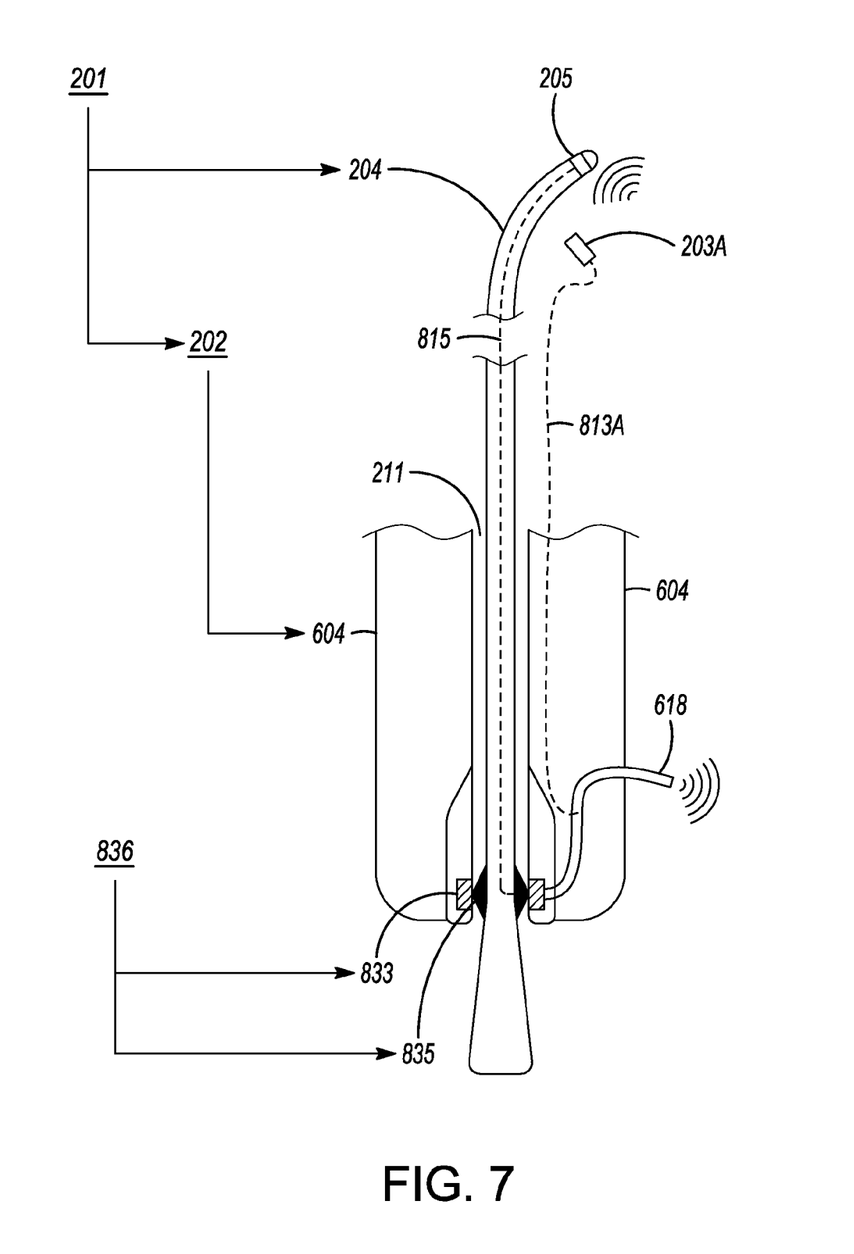
FIG. 7 depicts a schematic view of an embodiment of an energy-delivery assembly for use with the signal-interface assembly of the electroanatomical mapping system of FIG. 1.

FIG. 7 depicts a schematic view of an embodiment of an energy-delivery assembly 201 for use with the signal-interface assembly 901 of the electroanatomical mapping system 900 of FIG. 1. The view of FIG. 7 represents a longitudinal cross-sectional view of a portion of a medical dilator assembly 204 and a medical sheath assembly 202 (of the energy-delivery assembly 201).

Referring to the embodiment as depicted in FIG. 7, the medical sheath assembly 202 includes the handle extension 604. The sheath lumen 211 is defined through the handle extension 604 (or the medical sheath assembly 202). The sheath sensor 203A is positioned proximal to (close to) the dilator sensor 205. The medical dilator assembly 204 is received along the sheath lumen 211 of the medical sheath assembly 202. The dilator sensor 205 is mounted to the distal portion of the medical dilator assembly 204. The sheath wire assembly 618 exits from the handle extension 604 of the medical sheath assembly 202. The sheath wire assembly 618 provides a bundle of wires (conductors) to be electrically connected (either directly or indirectly) to the signal-interface assembly 901. The first electrical wire 813A is configured to convey the sensor signal of the sheath sensor 203A of the medical sheath assembly 202. The first electrical wire 813A merges with (or is connected to) a specific conductor of the sheath wire assembly 618. The second electrical wire 815 is configured to convey the sensor signal of the dilator sensor 205 of the medical dilator assembly 204.

Referring to the embodiment as depicted in FIG. 7, an electrical commutator device 836 is configured to convey the sensor signal of the second electrical wire 815 to a specific conductor of the sheath wire assembly 618. The electrical commutator device 836 (such as electrical commutator rings and contacts, etc., and any equivalent thereof) is configured to transfer electrical signals (and/or power) between a stationary element (such as the handle extension 604, etc.) and a movable and/or rotating shaft (such as the medical dilator assembly 204, etc.). The electrical commutator device 836 includes (preferably) a first electrical contact 833 mounted to the handle extension 604. The electrical commutator device 836 is configured for connecting the second electrical wire 815 to a dedicated wire of the sheath wire assembly 618 (via the electrical commutator device 836). The electrical commutator device 836 includes (preferably) a second electrical contact 835 mounted to the medical dilator assembly 204. The second electrical contact 835 is configured for the second electrical wire 815 (via the first electrical contact 833). The first electrical contact 833 and the second electrical contact 835 are configured to electrically contact each other while permitting relative movement between the medical dilator assembly 204 and the medical sheath assembly 202. It will be appreciated that an alternate embodiment (not depicted) provides an arrangement for a separate cable (wire) added for the dilator sensor 205, without the electrical commutator device 836.

Figure 8:
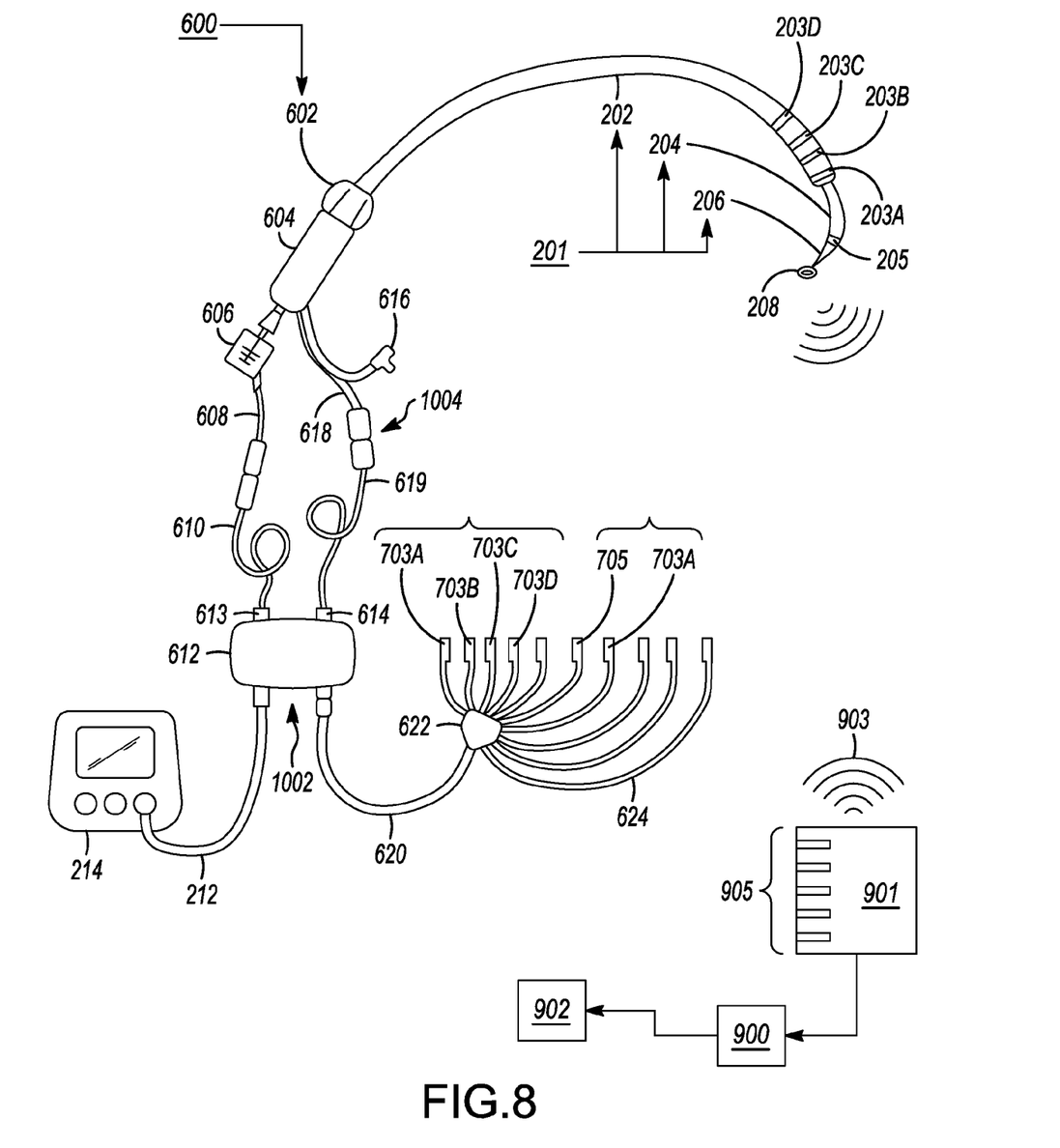
FIG. 8 depicts a schematic view of an embodiment of the signal-interface assembly of the electroanatomical mapping system of FIG. 1.

FIG. 8 depicts a schematic view of an embodiment of the signal-interface assembly 901 of the electroanatomical mapping system 900 of FIG. 1.

Referring to the embodiment as depicted in FIG. 8, there is provided a first internal jumper 1002 and a second internal jumper 1004. The internal jumpers (connections) are configured to transmit the dilator electrode signal from the dilator sensor 205 to the sheath wire assembly 618 (or to a sheath conductor cable 518, as depicted in FIG. 4). It will be appreciated that an alternate embodiment (not depicted) may be to provide a separate cable for the dilator sensor 205, etc.

Referring to the embodiment as depicted in FIG. 8, another arrangement to couple the sensors of the energy-delivery assembly 201 in the visualization on the mapping system is by using software (deployed on the electroanatomical mapping system 900). Since the mapping system software (of the electroanatomical mapping system 900) is configured to create (generate) the visualization (mapping information), the software may force the visualization map to be displayed to indicate improved coaxial alignment of the elements of the energy-delivery assembly 201, provided the software is programmed to identify the components of the energy-delivery assembly 201 (such as, dilator and sheath, etc.) and are connected in a specific physical manner or arrangement.

Referring to the embodiment as depicted in FIG. 8, it will be appreciated that assignment of the sensors of the energy-delivery assembly 201 (such as the dilator and sheath, etc.) may be accomplished separately in the mapping system software with shared sensors to model separate visualizations with different diameters, colours, etc., and/or a precisely aligned connection, such that the components of the energy-delivery assembly 201 may be displayed coaxially.

Referring to the embodiment as depicted in FIG. 8, it will be appreciated that visualization information of the elongated needle assembly 206, the medical dilator assembly 204 and/or the medical sheath assembly 202 in the visualization map (to be displayed in the display device 902) may be accomplished by way of the signal-interface assembly 901 (an intermediate platform) for combining the electrical connections.

Referring to the embodiment as depicted in FIG. 8, it will be appreciated that many other configurations may be possible for dedicated sensor conductors aligned along the energy-delivery assembly 201.

Referring to the embodiment as depicted in FIG. 8, it will be appreciated that the dilator signal may only be available when the dilator is locked into the hub in order to assure the spacing of inter-catheter electrodes is fixed.

Referring to the embodiment as depicted in FIG. 8, it will be appreciated that using multiple shared sensors (electrodes) between the catheters (the components of the energy-delivery assembly 201) to maintain a minimum of three electrodes for each individual catheter model may capture curvature and better accuracy of the tip vector.

Figure 9:
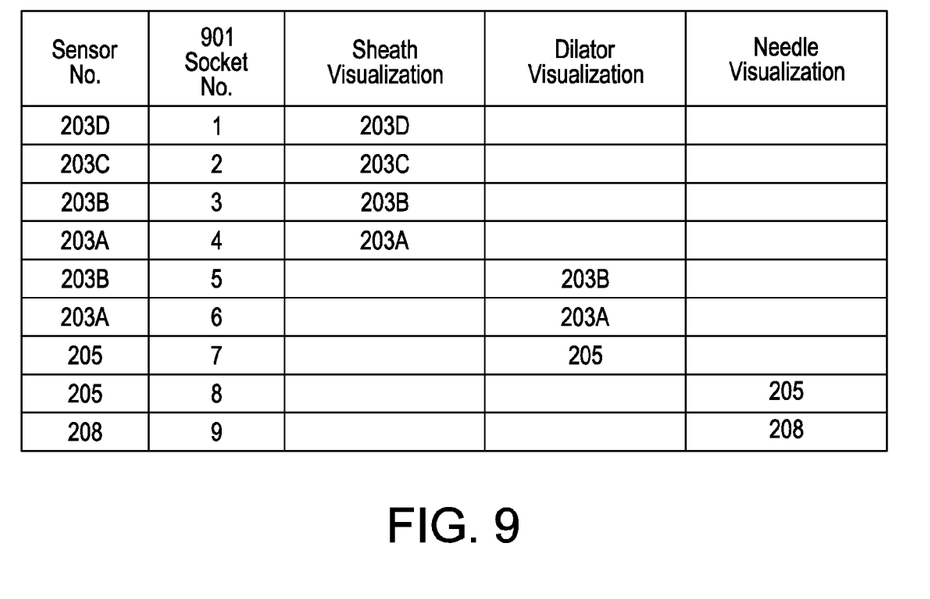
FIG. 9 depicts a schematic view of an embodiment of a configuration of the signal-interface assembly of FIG. 6 and/or FIG. 8.

FIG. 9 depicts a schematic view of an embodiment of a configuration of the signal-interface assembly 901 of FIG. 6 and/or FIG. 8.

Referring to the embodiment as depicted in FIG. 9, there is depicted an assignment between the pins and groupings for the sockets 905 of the signal-interface assembly 901 of FIG. 6 or of FIG. 8. It will be appreciated that other configurations for (assignment of) the grouping of pins may be realized, as desired, etc.

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure. The foregoing has outlined the non-limiting embodiments (examples). The description is made for particular non-limiting embodiments (examples). It is understood that the non-limiting embodiments are merely illustrative as examples.

What is claimed is:

1. An apparatus for use with an electroanatomical mapping system, an elongated needle assembly having a distal energy emitter configured to be detectable by the electroanatomical mapping system, an energy-delivery assembly having at least one sensor configured to receive, at least in part, the distal energy emitter of the elongated needle assembly in such a way that the distal energy emitter and said at least one sensor are movable relative to each other, the apparatus comprising:
   a signal-interface assembly including:
      a signal-input section configured to be signal connectable to said at least one sensor of the energy-delivery assembly; and
      a signal-output section configured to be signal connectable to an input section of the electroanatomical mapping system; and
      wherein the electroanatomical mapping system is configured to display, via a display device, spatial positions of said at least one sensor of the energy-delivery assembly along with the distal energy emitter of the elongated needle assembly after:
         the signal-input section, in use, is signal connected to said at least one sensor of the energy-delivery assembly; and
         the signal-output section, in use, is signal connected to the input section of the electroanatomical mapping system.

2. The apparatus of claim 1, wherein:
the energy-delivery assembly includes:
   a medical sheath assembly; and
   a medical dilator assembly configured to interact with the medical sheath assembly.

3. The apparatus of claim 1, wherein:
the energy-delivery assembly includes:
   an elongated needle assembly extending from the distal energy emitter, in which a wire is electrically connected to the distal energy emitter, and the wire extends along a length of the elongated needle assembly.

4. The apparatus of claim 3, wherein:
the energy-delivery assembly further includes:
   a medical sheath assembly configured to receive the elongated needle assembly, and the medical sheath assembly has at least one sheath sensor.

5. The apparatus of claim 4, wherein:
the energy-delivery assembly further includes:
   a medical dilator assembly configured to receive the medical sheath assembly, and the medical dilator assembly has at least one dilator sensor.

6. The apparatus of claim 1, wherein:
the signal-interface assembly is configured to receive at least one sensor signal from said at least one sensor of the energy-delivery assembly; and
the signal-interface assembly is also configured to convey, at least in part, said least one sensor signal to the electroanatomical mapping system.

7. The apparatus of claim 6, wherein:
the signal-interface assembly is configured to receive an energy signal associated with the energy-delivery assembly, and convey, at least in part, the energy signal to the electroanatomical mapping system.

8. The apparatus of claim 1, wherein:
the display device is configured to be electrically connected to the electroanatomical mapping system.

9. The apparatus of claim 8, wherein:
the electroanatomical mapping system is configured to output, in use, mapping information to the display device, in which the mapping information includes a spatial position of the distal energy emitter, once activated, and said at least one sensor of the energy-delivery assembly.

10. The apparatus of claim 1, further comprising:
a mapping cable configured to split into multiple conductors each having at least one dedicated pin electrically connected to at least one sensor of the energy-delivery assembly; and
the mapping cable also configured to interface with the signal-interface assembly.

11. The apparatus of claim 10, wherein:
the mapping cable includes at least one pin assigned into a grouping associated with an aspect of the energy-delivery assembly to be depicted on the display device.

12. The apparatus of claim 1, further comprising:
a mapping cable configured to split into multiple conductors each having at least one dedicated pin electrically connected to at least one sensor of the energy-delivery assembly.

13. The apparatus of claim 12, wherein:
the mapping cable is also configured to convey at least some of the energy signal from an energy generator to the signal-interface assembly.

14. The apparatus of claim 13, wherein:
the mapping cable is also configured to interface with the signal-interface assembly.

15. The apparatus of claim 1, wherein:
the signal-interface assembly is configured to electrically convey, in use, electrical signals from an aspect of the energy-delivery assembly.

16. The apparatus of claim 1, wherein:
the signal-interface assembly is configured to electrically convey, in use, electrical signals from an aspect of the energy-delivery assembly to enable visualization of aspects of the energy-delivery assembly via the display device of the electroanatomical mapping system.

17. The apparatus of claim 1, wherein:
the energy-delivery assembly includes:
an electrical commutator device configured to convey a sensor signal of at least one sensor of the energy-delivery assembly.

18. An apparatus for use with an electroanatomical mapping system including a signal-interface assembly, and also for use with an elongated needle assembly having a distal energy emitter configured to be detectable by the electroanatomical mapping system, the apparatus comprising:
an energy-delivery assembly having at least one sensor configured to receive, at least in part, the distal energy emitter of the elongated needle assembly in such a way that the distal energy emitter and said at least one sensor are movable relative to each other; and
said as least one sensor also configured to be interfaced to a signal-input section of the signal-interface assembly; and
the electroanatomical mapping system being configured to display, via a display device, spatial positions of said at least one sensor of the energy-delivery assembly along with the distal energy emitter of the elongated needle assembly after:
the signal-interface assembly, in use, is signal connected to said at least one sensor of the energy-delivery assembly; and
the signal-interface assembly, in use, is signal connected to the electroanatomical mapping system.

19. An apparatus, comprising:
an electroanatomical mapping system; and
an elongated needle assembly having a distal energy emitter configured to be detectable by the electroanatomical mapping system; and
an energy-delivery assembly having at least one sensor configured to receive, at least in part, the distal energy emitter of the elongated needle assembly in such a way that the distal energy emitter and said at least one sensor are movable relative to each other; and
a signal-interface assembly including:
a signal-input section configured to be signal connectable to said at least one sensor of the energy-delivery assembly; and
a signal-output section configured to be signal connectable to an input section of the electroanatomical mapping system; and
wherein the electroanatomical mapping system is configured to display, via a display device, spatial positions of said at least one sensor of the energy-delivery assembly along with the distal energy emitter of the elongated needle assembly after:
the signal-input section, in use, is signal connected to said at least one sensor of the energy-delivery assembly; and
the signal-output section, in use, is signal connected to the input section of the electroanatomical mapping system.

20. A method of operating an electroanatomical mapping system having a signal-interface assembly, an elongated needle assembly having a distal energy emitter configured to be detectable by the electroanatomical mapping system, an energy-delivery assembly having at least one sensor configured to receive, at least in part, the distal energy emitter of the elongated needle assembly in such a way that the distal energy emitter and said at least one sensor are movable relative to each other, the method comprising:
displaying, via the display device of the electroanatomical mapping system, spatial positions of said at least one sensor of the energy-delivery assembly along with the distal energy emitter of the elongated needle assembly after:
the signal-interface assembly, in use, is signal connected to said at least one sensor of the energy-delivery assembly; and
the signal-interface assembly, in use, is signal connected to the electroanatomical mapping system.

* * * * *